Figure 1:
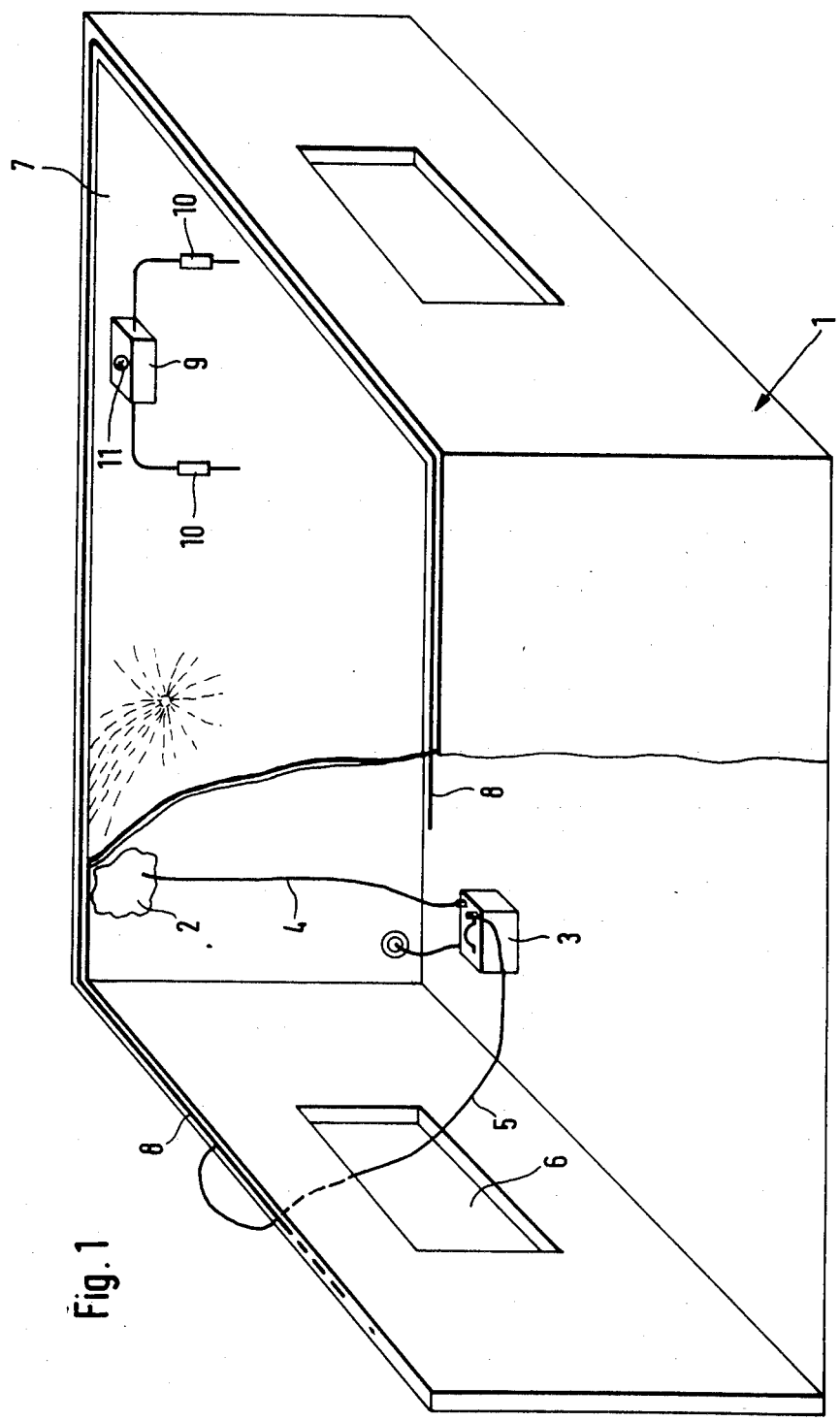

United States Patent [19]

Geesen

[11] Patent Number: 4,565,965
[45] Date of Patent: Jan. 21, 1986

[54] METHOD AND APPARATUS FOR LOCATING ROOF LEAKS IN FLAT ROOFS

[76] Inventor: Heinrich Geesen, Mootzenstrasse 24, 2915 Saterland 1, Fed. Rep. of Germany

[21] Appl. No.: 601,798

[22] Filed: Apr. 19, 1984

[30] Foreign Application Priority Data

Apr. 19, 1983 [DE] Fed. Rep. of Germany ....... 3314182

[51] Int. Cl.⁴ .......................................... G01R 27/02
[52] U.S. Cl. .................................. 324/65 R; 340/605
[58] Field of Search ............ 324/65 R; 340/605, 604; 200/61.04

[56] References Cited

U.S. PATENT DOCUMENTS 3,360,715 12/1967 Mueller ......................... 324/65 R X
3,823,304 7/1974 Siemianowski .............. 200/61.04 X Primary Examiner—Stanley T. Krawczewicz
Attorney, Agent, or Firm—Collard, Roe & Calgano

[57] ABSTRACT

There is provided a method and apparatus for locating leaks in flat roofs, particularly in flat roofs covered with a gravel layer, plants or the like, and wherein it is provided that a moisture location discovered below the flat roof is connected with a positive terminal of a pulse generator, the negative terminal of the pulse generator being connected with a metallic gutter edge of the flat roof, and the flat roof being scanned by measurement sensors for the purpose of measuring the pulses passing through the moisture path to the corresponding leak location and from the leak location through the moist, flat roof. The measurement sensors are connected with a measurement device for measuring the impulse amplitudes, which become successively weaker as they progress from the leak location to the rim of the flat roof.

6 Claims, 2 Drawing Figures

METHOD AND APPARATUS FOR LOCATING ROOF LEAKS IN FLAT ROOFS

The present invention relates to a method and apparatus for locating leaks in flat roofs, particularly flat roofs covered with gravel, plants or the like.

Flat roofs generally include as roofing, roof tar paper, which may be glued or nailed together in several layers. In order to provide heat insulation, such roofs are frequently covered by a heat-insulating gravel layer. In order to discover any leaks in flat roofs, the person laying the roof must examine the roof visually. During such examination the person laying the roof inspects those locations which are frequently endangered, according to their experience. It is particularly difficult to find roof leaks in flat roofs which are covered with a layer of gravel, since the leak locations are covered by the layer of gravel. In such situations it is necessary to first remove the layer of gravel. Furthermore, if such leaks are relatively small, then such a search very often lasts several days. This may be true even in the case of flat roofs which are not provided with gravel layers.

It is, therefore, an object of the present invention to provide a method and apparatus which permits a rapid and simple location of leaks in flat roofs.

This object, as well as others which will hereinafter become apparent, is accomplished according to the present invention by connecting the positive terminal of a pulse generator to a moisture location discovered below the flat roof, the negative terminal of the pulse generator being connected to the metal gutter edge of the flat roof, and the flat roof being scanned by means of measurement sensors. The measurement sensors measure the pulses which are fed through a moisture path to the corresponding leak location, and from the leak location through the moist flat roof to the metal edge thereof. The measurement sensors are in turn connected to a measurement apparatus, which measures the pulse amplitudes which become weaker or are attenuated as the sensors progress from the leak location to the rim of the flat roof.

By means of the present method, electrical pulses from the pulse generator pass through the moisture path from the moisture location to the leak location, as well as through the moist flat roof to the edge thereof. The pulses have the greatest pulse amplitudes at the leak location. The magnitude of the pulse amplitudes decreases in the direction towards the rim of the flat roof. Consequently, an operator can measure the pulse amplitudes, which increase in the direction towards the leak location, by means of a measurement device equipped with measurement sensors which sense the pulses and transmit them to the measurement device. The operator progresses along the direction of the largest value of the pulse amplitudes indicated by the measurement device, so that he follows the pulse amplitudes as they increase towards the leak location, until the leak location has been discovered. By means of this simple and advantageous manner, leak locations can be discovered relatively quickly and simply. By this method, the demand for personnel during a search for leak locations is reduced to a minimum, so that repairs of flat roofs can be accomplished at a considerably lower cost.

If no metallic gutter edge is provided on the flat roof, according to the present invention, the negative terminal of the pulse generator is connected to a blank cable laid out on the flat roof. In this manner, the electrical circuit from the positive terminal to the negative terminal of the pulse generator is closed in a simple fashion.

The apparatus for carrying out the above described method includes a pulse generator which generates direct current pulses, and a measurement apparatus which compares pulse amplitudes fed thereto through measurement sensors. The largest pulse amplitude is displayed as a center zero indication on a display scale instrument. As a result of the zero center indication of the display scale instrument, the pulse amplitudes which increase in the direction towards the leak location are indicated by the pointer of the instrument, so that an operator need only follow the direction of the deflection of the pointer, until the pointer assumes its center position, namely its zero position. The leak location is located thereat, as the magnitude of the pulse amplitudes is about equal at the region of the leak location, so that approximately equal pulse amplitudes are fed to the measurement instrument, which in turn will not cause any deflection of the pointer of the display scale instrument. By this means, location of leaks in flat roofs is simplified or improved.

As a further development of the apparatus, the measurement sensors are partially insulated aluminum rods which are connected with the bases of two transistors connected as a difference amplifier, the emitters of the two transistors being connected to one another through the display scale instrument. In this way, the relatively small pulse amplitudes measured by the measurement sensors, are amplified by the transistors and fed to the display scale instrument. Because the transistors are connected as a difference amplifier, the pointer of the display scale instrument is deflected to the left or right depending on the respective larger pulse amplitude, or it remains in its center position if the two pulse amplitudes are constant.

Other objects and features of the present invention will become apparent from the following detailed description considered in connection with the accompanying drawings. It is to be understood, however, that the drawings are designed as an illustration only and not as a definition of the limits of the invention.

Figure 2:
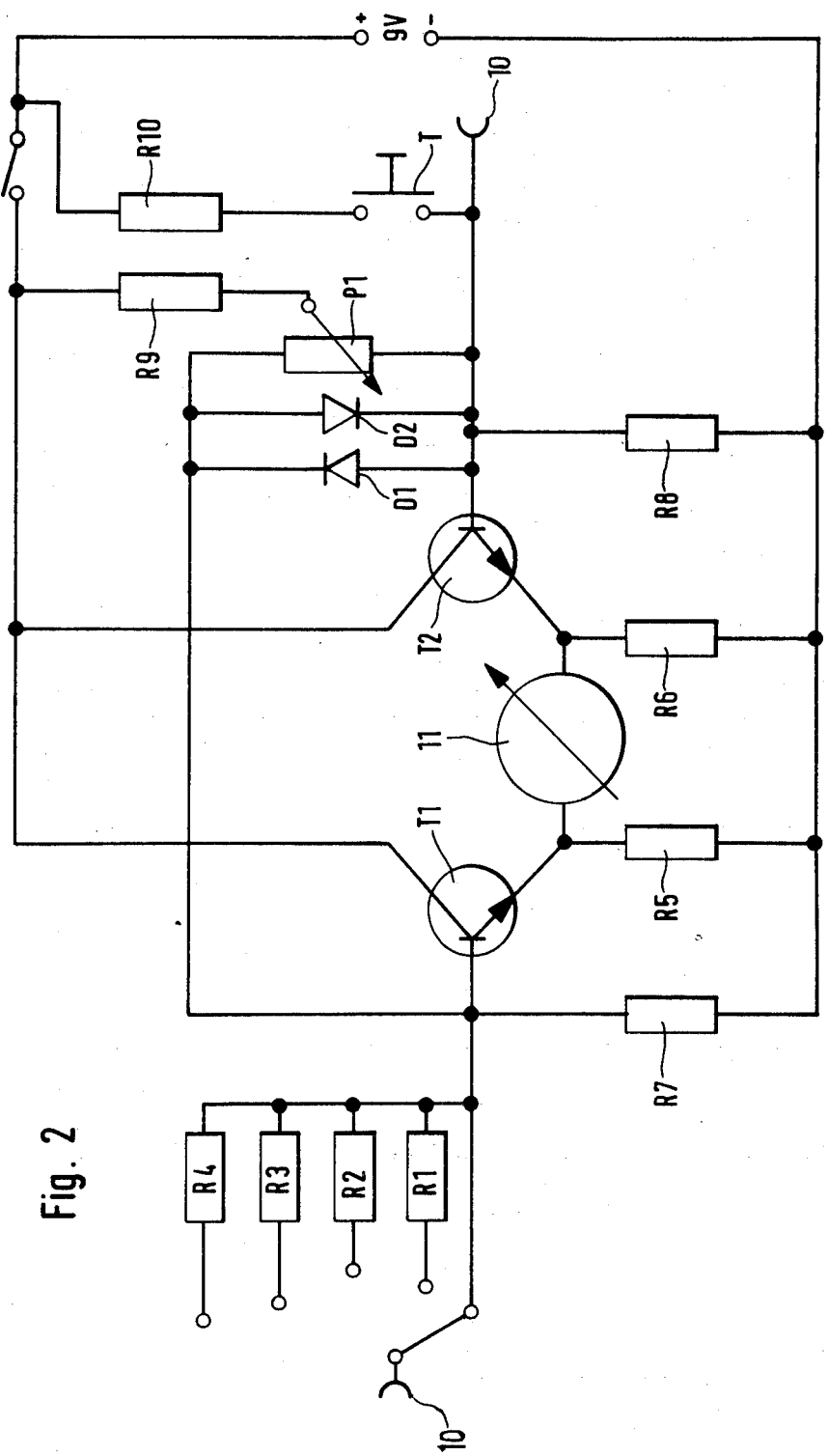

In the drawings wherein similar reference characters denote similar elements throughout the several views:

FIG. 1 is a schematic perspective view of a house, partly broken away, including a pulse generator and a measuring instrument; and FIG. 2 is an electrical circuit diagram of the measurement instrument.

Now turning to the drawings, there is shown in FIG. 1 a house 1 having a moisture location 2 caused by a leak in the flat roof 7, through which water has penetrated. A pulse generator 3 is connected with the lead of its positive terminal 4 to the moisture location. The negative terminal 5 of pulse generator 3 is connected with its lead through a window 6 to a cable or metal gutter 8 surrounding flat roof 7. Pulse generator 3 is connected to the electrical supply of the house and, upon being switched on, transmits direct-current pulses which pass from the moisture location through the moisture path to the leak location and from there through the wet or moistened flat roof to the blank cable 8, thereby returning to the pulse generator, and closing the current circuit. These pulses or pulse amplitudes, which are attenuated as they progress to the rim of flat roof 7, may be measured by measuring apparatus 9 by scanning the roof by means of measurement sensors 10.

Measurement apparatus 9 is provided with a display scale instrument 11 having a central zero position. Display scale instrument 11 is connected in a circuit as illustrated in FIG. 2, and the pointer thereof is deflected left or right depending upon the measured magnitude of the pulse amplitudes and indicates the largest measured pulse amplitude. Consequently, there is shown simultaneously the direction of the pulse amplitudes, which become greater as the leak location is approached. Display scale instrument 11 is connected to the emitters of transistors T1 and T2, connected as a difference amplifier. The bases of the two transistors are connected to measurement sensors 10. The pulse amplitudes sensed by measurement sensors 10 are therefore fed as input signals to transistors T1 and T2, are amplified by them and are supplied to display scale instrument 11 in the emitter circuit. Display scale instrument 11 measures the current of the emitters of the transistors T1 and T2, the emitters being connected to one another, and therefore is deflected leftwardly or rightwardly depending upon which transistor carries the larger current. If both currents are equal, no deflection occurs. Display scale instrument 11 may be equalized to its center position through collector resistor R9 and adjustable resistor P1, so that its pointer is set to the center position. Furthermore, in the input circuit, two diodes D1 and D2 are disposed, which protect transistors T1 and T2 from high voltages. Furthermore, resistors R1 through R4 are precoupled to the input circuit as precoupling resistors, by means of which the sensitivity of the measurement instrument can be set. The circuit is fed by a 9 volt D.C. dry cell battery. In order to examine the charged state of the battery, a key T is provided, which effects a deflection of the display scale instrument through a resistor R10, if the dry cell battery is well charged. Resistors R5 and R6 are emitter resistors for transistors T1 and T2, respectively. The bases of the transistors are connected to ground through resistors R7 and R8, respectively, so that a symmetrical feed of the transistors or of the difference amplifier, respectively, is accomplished.

While only a single embodiment of the present invention has been shown and described, it will be obvious that many changes and modifications may be made thereto without departing from the spirit and scope of the invention.

What is claimed is:

1. A method for locating roof leaks in a flat roof, comprising the steps of:
   connecting the positive terminal of a pulse generator to a moisture location below the flat roof;
   connecting the negative terminal of the pulse generator to a metal gutter edge of the roof;
   detecting pulses fed through the moisture path from the moisture location to the leak location and to the metal gutter by measurement sensors; and
   measuring the pulse amplitudes by means of a measurement apparatus connected to said measurement sensors, the pulse amplitudes attenuating in a direction away from the leak location towards the edge of the flat roof.

2. The method for locating roof leaks in a flat roof as defined in claim 1, wherein the negative terminal of the pulse generator is connected to a cable surrounding the flat roof.

3. Apparatus for locating roof leaks in a flat roof surrounded by a metal cable, comprising:
   a pulse generator for generating direct current pulses having positive and negative terminals, the positive terminal being connected to the moisture location below the flat roof and the negative terminal being connected to the metal cable surrounding the roof;
   two measurement sensors for detecting the pulses fed through the moisture path from the moisture location to the leak location and to the metal cable surrounding the flat roof generated by said pulse generator; and
   measurement apparatus for comparing the pulse amplitudes received from said sensors and displaying the larger pulse amplitude through a display scale instrument having a zero center indication.

4. The apparatus as defined in claim 3, wherein the sensors are partially insulated aluminum rods each connected to the base of a transistor, the two transistors being connected to form a difference amplifier, and the emitters of the transistors being connected to one another through the display scale instrument of said measurement apparatus.

5. Apparatus for locating roof leaks in a flat roof surrounded by a metal gutter, comprising:
   positive and negative terminals, the positive terminal being connected to the moisture location below the flat roof and the negative terminal being connected to the metal gutter surrounding the roof;
   two measurement sensors for detecting the pulses fed through the moisture path from the moisture location to the leak location and to the metal gutter surrounding the flat roof generated by said pulse generator; and
   measurement apparatus for comparing the pulse amplitudes received from said sensors and displaying the larger pulse amplitude through a display scale instrument having a zero center indication.

6. The apparatus as defined in claim 5, wherein the sensors are partially insulated aluminum rods each connected to the base of a transistor, the two transistors being connected to form a difference amplifier, and the emitters of the transistors being connected to one another through the display scale instrument of said measurement apparatus.

* * * * *